US010358662B2

(12) United States Patent
Simpson et al.

(10) Patent No.: US 10,358,662 B2
(45) Date of Patent: Jul. 23, 2019

(54) INTEGRATED FERMENTATION AND ELECTROLYSIS PROCESS

(71) Applicant: LanzaTech New Zealand Limited, Skokie, IL (US)

(72) Inventors: Sean Dennis Simpson, Skokie, IL (US); Robert John Conrado, Skokie, IL (US); Christophe Daniel Mihalcea, Skokie, IL (US); Michael Emerson Martin, Skokie, IL (US)

(73) Assignee: LANZATECH NEW ZEALAND LIMITED, Skokie, IL (US)

( * ) Notice: Subject to any disclaimer, the term of this patent is extended or adjusted under 35 U.S.C. 154(b) by 70 days.

(21) Appl. No.: 15/422,424

(22) Filed: Feb. 1, 2017

(65) Prior Publication Data
US 2017/0218404 A1 Aug. 3, 2017

Related U.S. Application Data

(60) Provisional application No. 62/289,900, filed on Feb. 1, 2016.

(51) Int. Cl.
*C12P 7/06* (2006.01)
*C25B 1/04* (2006.01)
(Continued)

(52) U.S. Cl.
CPC ............. *C12P 7/065* (2013.01); *C12M 43/00* (2013.01); *C12M 45/07* (2013.01); *C12P 7/16* (2013.01);
(Continued)

(58) Field of Classification Search
CPC ... C12N 1/20; C12N 9/16; C12N 1/12; C12N 1/14; C12N 1/16; C12N 9/0008; C12N 9/001; C12N 9/1029; C12N 9/93; C12N 15/00; C12N 15/63; C12N 9/18; C10L 1/02; C10L 1/026; C10L 1/19; C12P 7/649; C12P 7/6409; C12P 7/6436; C12P 7/6463; C12P 21/06; C12P 7/065; C12P 1/04; C12P 3/00; C12P 5/023; C12P 7/08; C12P 7/16; C12P 7/40; C12P 7/54; C12P 7/625; C12P 7/06; C12P 7/18; C12P 39/00; C12P 7/52; C12P 7/6427; C12P 7/6472; C12P 5/02; C12P 7/14; Y02E 50/13; Y02E 50/343; Y02E 50/17; Y02E 60/366; Y02E 20/326; Y02E 50/346; Y02E 50/10; Y02E 20/133; A61B 5/14532; A61B 5/14865; A61B 5/14546; A61B 5/1495; A61B 5/6833; A61B 5/1486; A61B 5/1473; A61B 5/742; A61B 2560/0223; A61B 2560/0276; A61B 2560/028; A61B 5/0031; A61B 5/1451; A61B 5/14517; A61B 5/1468; A61B 5/6832; A61B 5/6848; A61B 5/6849; A61B 5/7264; A61B 5/0004; A61B 5/7207; A61B 17/3468; A61B 2017/3492; A61B 2560/045; A61B 2562/18; A61B 5/14503; A61B 5/14507; A61B 5/6801; A61B 5/002; A61B 5/1411; A61B 5/15142; A61B 5/72; A61B 5/746; C07C 69/34; C07C 69/52; C07C 69/533; C11C 3/003; C12M 43/04; C12M 29/02; C12M 29/18; C12M 29/20; C12M 23/34; C12M 23/40; C12M 25/00; C12M 29/08; C12M 29/24; C12M 41/44; C12M 41/46; C12M 41/48; C12M 47/02; C12M 43/00; C12M 45/07; C12M 21/04; C12M 43/06; C12Y 102/01; C12Y 301/02; C12Y 602/01; C12Y 604/01; Y02A 90/22; Y02A 90/26; Y02A 50/2358; C07H 21/04; C25B 1/04; C25B 15/02; C25B 15/08; C25B 1/00; C25B 1/003; Y02P 20/133; Y02P 20/152; Y02P 20/59; Y02P 30/10; Y02P 30/20; Y02P 30/446; Y02P 20/132; Y02P 20/146; A61L 2/12; A61L 2/206; G06F 19/00; Y10T 29/49004; G16H 40/40; Y02W 30/47; B01D 2251/95; B01D 2257/504; B01D 53/62; B01D 53/84; C10G 2300/1011; C10G 2300/4043; C10G 2300/405; C10G 11/18; C10G 2300/708;
(Continued)

(56) References Cited

U.S. PATENT DOCUMENTS 9,085,785 B2 * 7/2015 Reed ..................... C12N 1/12
9,157,058 B2 * 10/2015 Dalla-Betta ............ C12M 29/02
(Continued)

OTHER PUBLICATIONS

Cotter et al Infl. of process parameaters on growth of Clostridum Ljungdahlii and C. autoethanogenum on syn gas. Enz. and Micr. Tech. May 6, 2009; 44(5): 281-8.*

*Primary Examiner* — Deborah K Ware
(74) *Attorney, Agent, or Firm* — James A Edwards

(57) ABSTRACT

The invention provides schemes for the integration of a fermentation process, with an electrolysis process, and a C1-generating industrial process. In particular, the invention provides process for utilizing electrolysis products, for example $H_2$ and/or $O_2$, to improve the process efficiency of at least one of the fermentation process or the C1-generating industrial process. More particularly, the invention provides a process whereby, $H_2$ generated by electrolysis is used to improve the substrate efficiency for a fermentation process, and the $O_2$ generated by the electrolysis process is used to improve the composition of the C1-containing tail gas generated by the C1-generating industrial process.

17 Claims, 2 Drawing Sheets

(51) Int. Cl.
  *C25B 1/00* (2006.01)
  *C12M 1/00* (2006.01)
  *C25B 15/08* (2006.01)
  *C12P 7/16* (2006.01)
  *C12P 7/18* (2006.01)
  *C12P 7/54* (2006.01)

(52) U.S. Cl.
  CPC .................................. *C12P 7/18* (2013.01);
    *C12P 7/54* (2013.01); *C25B 1/00* (2013.01);
    *C25B 1/003* (2013.01); *C25B 1/04* (2013.01);
    *C25B 15/08* (2013.01); *Y02E 50/17* (2013.01);
    *Y02E 60/366* (2013.01); *Y02P 20/133* (2015.11)

(58) Field of Classification Search
  CPC .......... C10G 9/36; F23J 15/02; F23J 2215/50;
    Y02C 10/02; Y02C 10/04; C10B 2203/0233; C10B 2203/0283; C10B 2203/043; C10B 2203/06; C10B 2203/061; C10B 2203/1058; C10B 3/38; C10J 3/38; C10J 2300/0943; C10J 2300/1681; C10J 2300/1846; C10K 3/026; G01N 33/92; A23K 10/12; C12R 1/02; C12R 1/145
  See application file for complete search history.

(56) References Cited

U.S. PATENT DOCUMENTS

| | | | |
|---|---|---|---|
| 2010/0120104 A1* | 5/2010 | Reed | C12P 7/40 435/140 |
| 2012/0003705 A1* | 1/2012 | Jin | B01D 53/62 435/136 |
| 2013/0078690 A1* | 3/2013 | Reed | C12P 7/54 435/140 |
| 2013/0189763 A1* | 7/2013 | Dalla-Betta | C12M 29/02 435/252.1 |
| 2016/0102287 A1* | 4/2016 | Dalla-Betta | C12M 29/02 435/134 |

\* cited by examiner

INTEGRATED FERMENTATION AND ELECTROLYSIS PROCESS

CROSS REFERENCE TO RELATED APPLICATIONS

This application claims the benefit of U.S. Provisional Patent Application No. 62/289,900 filed Feb. 1, 2016, the entirety of which is incorporated herein by reference.

BACKGROUND OF THE INVENTION

Carbon dioxide ($CO_2$) accounts for about 76% of global greenhouse gas emissions from human activities, with methane (16%), nitrous oxide (6%), and fluorinated gases (2%) accounting for the balance (United States Environmental Protection Agency). The majority of $CO_2$ comes from the burning fossil fuels to produce energy, although industrial and forestry practices also emit $CO_2$ into the atmosphere. Reduction of greenhouse gas emissions, particularly $CO_2$, is critical to halt the progression of global warming and the accompanying shifts in climate and weather.

It has long been recognized that catalytic processes may be used to convert gases containing carbon dioxide ($CO_2$), carbon monoxide (CO), and/or hydrogen ($H_2$), such as industrial waste gas or syngas, into a variety of fuels and chemicals. Recently, however, gas fermentation has emerged as an alternative platform for the biological fixation of such gases. In particular, C1-fixing microorganisms have been demonstrated to convert gases containing $CO_2$, CO, and/or $H_2$ into products such as ethanol and 2,3-butanediol. Efficient production of such products may be limited, for example, by slow microbial growth, limited gas uptake, sensitivity to toxins, or diversion of carbon substrates into undesired by-products.

It has long been recognized that catalytic processes, such as the Fischer-Tropsch process, may be used to convert gases containing carbon dioxide ($CO_2$), carbon monoxide (CO), and/or hydrogen ($H_2$) into a variety of fuels and chemicals. Recently, however, gas fermentation has emerged as an alternative platform for the biological fixation of such gases. In particular, anaerobic C1-fixing microorganisms have been demonstrated to convert gases containing $CO_2$, CO, and/or $H_2$ into products, like ethanol and 2,3-butanediol.

Such gasses may be derived, for example, from industrial processes, including ferrous or non-ferrous metal products manufacturing, petroleum refining, gasification, electric power production, carbon black production, ammonia production, methanol production, and coke manufacturing. However, these industrial gasses may require treatment or recomposition to be optimized for use in gas fermentation systems. In particular, industrial gasses may lack sufficient amounts of $H_2$ to drive net fixation of $CO_2$ by gas fermentation and reduce $CO_2$ emissions to the atmosphere.

High hydrogen streams are beneficial to fermentation products which have low energy demand and where $CO_2$ can be used as a reactant, such as with ethanol production.

Accordingly, there remains a need for improved integration of industrial processes with gas fermentation systems, including processes for enriching the $H_2$ content of industrial gases delivered to gas fermentation systems.

SUMMARY OF THE INVENTION

The invention provides a process for improving carbon capture in an integrated fermentation and industrial process, wherein the method comprises passing one or more feedstocks to an electrolysis process to produce an electrolysis derived substrate, blending at least a portion of the electrolysis derived substrate with a C1-containing tail gas from an industrial process to provide a blended C1-containing gaseous substrate, passing the blended C1-containing gaseous substrate to a bioreactor containing a culture of at least one C1-fixing bacterium, and fermenting the culture to produce at least one fermentation product. In a preferred embodiment, the electrolysis derived substrate comprises at least one electron source and/or at least one carbon source.

Preferably, the electrolysis derived substrate comprises CO or $H_2$. Preferably, the electrolysis derived substrate further comprises $O_2$, wherein said $O_2$ is utilized to improve the efficiency of the industrial process. In one embodiment the electrolysis derived substrate comprises $H_2$ and $O_2$, and is derived from a water electrolysis process. In an alternative embodiment, the electrolysis derived substrate comprises CO and $O_2$, and is derived from a $CO_2$ electrolysis process. In one embodiment the energy input for the electrolysis process is a renewable energy source selected from the group consisting of wind power, hydropower, solar power, nuclear power and geothermal power.

The industrial process is selected from the group consisting of partial oxidation processes and complete oxidation processes, Exemplary partial oxidation processes include Basic oxygen furnace (BOF) reactions; COREX or FINEX steel making processes, Blast Furnace (BF) processes, ferroalloy processes, titanium dioxide production processes and gasification processes. Complete oxidation processes include natural gas power processes, coal fired power processes, and cement production processes.

In certain embodiments, a portion of the C1-containing tail gas is blended with a portion of the oxygen from the electrolysis unit to match the oxygen richness required for the feed to the industrial process.

The fermentation product(s) is selected from the group consisting of ethanol, acetate, butanol, butyrate, 2,3-butanediol, lactate, butene, butadiene, methyl ethyl ketone, ethylene, acetone, isopropanol, lipids, 3-hydroxypropionate, isoprene, fatty acids, 2-butanol, 1,2-propanediol, and 1-propanol.

The invention further provides an integrated process for producing one or more products, the process comprising; producing hydrogen by electrolysis, blending at least a portion of the produced hydrogen stream with a gaseous stream comprising at least $CO_2$, passing the blended stream to a bioreactor containing a culture of at least one C1 fixing bacterium, and fermenting the culture to produce one or more products.

Preferably, the renewable hydrogen stream is produced by electrolysis of water. In certain embodiments the electrolysis process produces $O_2$ as a by-product. Preferably, the gaseous stream comprising at least $CO_2$ is produced by a complete oxidation processes. Examples of complete oxidation processes include, but are not limited to natural gas power plants, coal fired power plants, and cement production processes.

The invention further provides a process for producing one or more products from a gaseous substrate comprising renewable hydrogen, the process comprising: receiving a first gaseous substrate comprising renewable hydrogen, and a second gaseous substrate comprising $CO_2$, passing at first portion of hydrogen and a first portion of $CO_2$ to a reverse water gas shift reactor operated under conditions to produce an exit stream comprising CO, blending a second portion of hydrogen, a second portion of $CO_2$ and the exit stream comprising CO to provide a blended C1-containing substrate, passing the blended C1-containing substrate to a bioreactor containing a culture of one or more C1 fixing bacterium, and fermenting the culture to produce one or more products. Preferably, the renewable hydrogen is produced by electrolysis of a renewable energy source. In one embodiment the substrate comprising $CO_2$ is produced by an industrial process. In a preferred embodiment, the industrial process is a cement production process.

Further, there is provided an integrated system comprising; a C1-generating industrial process zone, an electrolyser, and a C1 fixing fermentation zone. The integrated system has the benefit of producing a valuable carbon containing product from a C1 waste gas, and reducing $CO_2$ emissions. The provision of an electrolyser for the electrolysis of water or carbon dioxide also reduces the requirement for air separation by alternative means, as $O_2$ produced by the electrolysis process can replace or supplement $O_2$ requirements of the industrial process.

In one embodiment, the integrated system further comprises a blending zone, for blending a portion of an electrolysis derived substrate with at least a portion of a C1-containing tail gas from the C1-generating industrial process zone to produce a blended C1-containing substrate. The integrated system further comprises a conduit for passing the blended C1-containing substrate from the blending zone to the C1-fixing fermentation zone.

In a one embodiment, energy input for the electrolyser is provided by a renewable energy production zone. The renewable energy production zones may comprise at least one technology selected from the group consisting of wind power, hydropower, solar power, nuclear power and geothermal power.

DETAILED DESCRIPTION OF THE INVENTION

Figure 1:
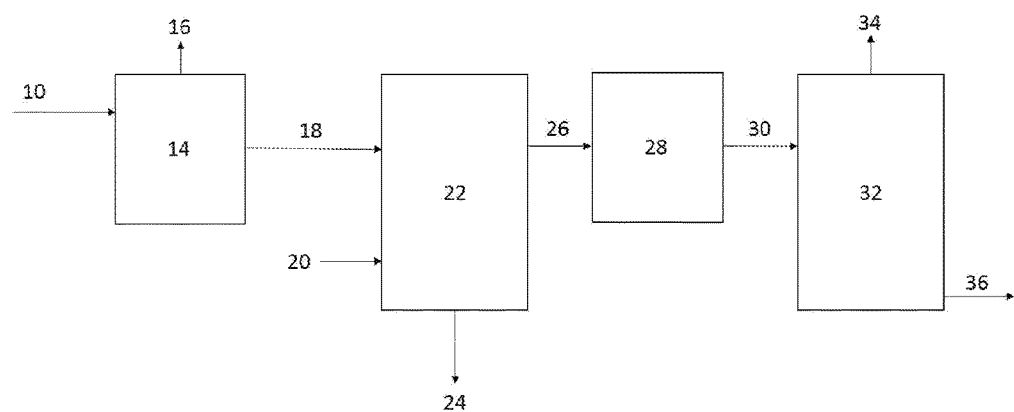
FIG. 1 shows a process integration scheme depicting integration of a Basic Oxygen Furnace process with a fermentation process.

The inventors have identified that the integration of a C1-generating industrial process with a C1-fixing fermentation process, and an electrolysis process provides substantial benefits to the C1-generating industrial process, and the C1-fixing fermentation process.

A "C1-generating industrial process" is an industrial process which generates at least one C1-containing gas during its operation process. The C1-generating industrial process is intended to include any industrial process which generate a C1-containing gas as either a desired end product, or as a by-product in the production of one or more desired end products. Exemplary C1-generating industrial processes include, but are not limited to, steel manufacturing process, including Basic oxygen furnace (BOF) processes; COREX or FINEX steel making processes, Blast Furnace (BF) processes and Coke Oven Gas processes, gasification processes, including, gasification of municipal solid waste, biomass gasification, gasification of lignin and associated streams, pet coke gasification and coal gasification, titanium dioxide production processes, cement production processes, natural gas power processes and coal fired power processes.

A "desired end product" is intended to encompass the primary or target product of the industrial process. For example, the desired end product of a steel manufacturing process is a steel product, and a C1-containing gas is generated as a by-product, however in a MSW gasification process, syngas, a C1-containing gas is the desired end product of the gasification process.

Hydrogen is a particularly suitable source of energy for fermentation processes. The inventors have found a number of synergistic benefits to integration of a hydrogen producing electrolysis process with both a C1-generating industrial process and a C1-fixing fermentation process. More particularly, the inventors have discovered that the electrolysis process can be coupled with a C1-generating industrial process, to improve the composition of C1-containing gases generated by the industrial process.

Hydrogen can be produced by an electrolysis process, defined by the following stoichiometric reaction:

$$2H_2O + electricity \rightarrow 2H_2 + O_2 + heat$$

Water electrolysis technologies are known in the art. Exemplary processes include alkaline water electrolysis, protein exchange membrane (PEM) electrolysis, and solid oxide electrolysis. Suitable electrolysers include Alkaline electrolysers, PEM electrolysers, and solid oxide electrolysers (Ursua et al, Hydrogen Production From Water Electrolysis: Current Status and Future Trends, In: Proceedings of the IEEE100(2):410-426, February 2012). The Hydrogen produced by electrolysis can be used as a feedstock for gas fermentation when supplied in combination with industrial waste gases containing a suitable carbon source e.g. at least one C1 containing gas, such as Carbon monoxide (CO) and/or Carbon dioxide ($CO_2$).

Additionally it is considered that the produced hydrogen can be blended with an industrial gas stream comprising at least a portion of hydrogen, as a means to supply additional feedstock and to improve substrate composition. Substrate composition can be improved to provide a desired or optimum $H_2:CO:CO_2$ ratio. The desired $H_2:CO:CO_2$ ratio is dependent on the desired fermentation product of the fermentation process. For ethanol, the optimum $H_2:CO:CO_2$ ratio would be:

$$(x):(y):\left(\frac{x-2y}{3}\right),$$

where x>2y, in order to satisfy the stoichiometry for ethanol production $$(x)H_2 + (y)CO + \left(\frac{x-2y}{3}\right)CO_2 \rightarrow \left(\frac{x+y}{6}\right)C_2H_5OH + \left(\frac{x-y}{2}\right)H_2O.$$

Alternatively carbon monoxide and oxygen can be produced by an electrolysis process, defined by the following stoichiometric reaction: $2CO_2 + electricity \rightarrow 2CO + O_2 + heat$. The carbon monoxide produced by electrolysis can be used as a feedstock for gas fermentation. Additionally it is considered that the produced CO can be blended with an industrial gas stream, as a means to supply additional feedstock.

Electrolysis processes and electrolysers the reduction of $CO_2$ are known. The use of different catalysts for $CO_2$ reduction impact the end product. Catalysts including Au, Ag, Zn, Pd, and Ga catalysts have been shown effective for the production of CO from $CO_2$. Standard electrolysers, such as those described above for water electrolysis can be used. (Thong et al; Electrochemical conversion of $CO_2$ to useful chemicals: current status, remaining challenges, and future opportunities, In: Science Direct; Current Opinion in Chemical Engineering 2013, 2:191-199).

Surprisingly, the inventors have identified that the $O_2$ by-product of the electrolysis processes described above provides additional benefit to the use of industrial gas for fermentation. Whilst the fermentation processes of the current invention are anaerobic processes, the inventors have identified that the $O_2$ by-product of the both the hydrogen production process and CO production process can be used in the C1-generating industrial process from which the C1-containing tail gas is derived. The high-purity $O_2$ by-product of the electrolysis process can be integrated with the industrial process and beneficially offset costs and in some cases have synergy that further reduces costs for both the industrial process as well as the subsequent gas fermentation.

Typically, the industrial processes described herein derive the required oxygen by air separation. Production of oxygen by air separation is an energy intensive process which involves cryogenically separating $O_2$ from $N_2$ to achieve the highest purity Co-production of $O_2$ by electrolysis, and displacing $O_2$ produced by air separation, could offset up to 5% of the electricity costs in an industrial process. For example, an electrolysis process can consume 224 kWh/kmol $O_2$, based on 5 kWh electricity consumption per Nm3 of $H_2$ produced. This compares to modern air separation units which consume 300 kWh per tonne of high purity of $O_2$ produced, 9.6 kWh/kmol $O_2$ produced. Additionally, the provision of a high purity $O_2$ source enriches the C1-gas containing tail gas produced by the industrial process, thereby providing a more efficient C1-containing substrate for fermentation. For example, a typical BOF tail gas contains approximately 20% nitrogen (typical BOF tail gas composition is 60% $CO_3$ 20% $CO_2$, 20% $N_2$). The $N_2$ in the BOF stream is a result of the $O_2$ feed to the BOF process, which is typically 94% $O_2$ and 6% $N_2$. In a case where 100,000 Nm3/h of BOF gas is produced, and the BOF stream is supplemented with enough $H_2$ for total carbon capture (approx. 180,000 Nm3/h $H_2$), said hydrogen being produced by electrolysis of water, the available $O_2$ from the electrolysis process, when sent to the BOF process to displace the typical feed of 94% $O_2$/6% $N_2$, would reduce the $N_2$ composition in the resultant BOF gas by approx. 57%. In certain embodiments of the invention, there is provided a process for reducing nitrogen concentration in a C1-containing tail gas, the process comprising displacing a typical BOF process $O_2$ feed, with a high purity $O_2$ stream derived from a water electrolysis process. In certain embodiments, the nitrogen concentration in the C1-containing tail gas is reduced by at least 20%, or at least 30%, or at least 40%, or at least 50%, or at least 55%, compared to a process where the typical $O_2$ feed is not displaced.

A number of C1-generating industrial processes involving partial oxidation reactions, require an $O_2$ input. Exemplary industrial process include Basic oxygen furnace (BOF) reactions; COREX or FINEX steel making processes, Blast Furnace (BF) processes, ferroalloy production processes, titanium dioxide production processes, and gasification processes. Gasification processes include, but are not limited to municipal solid waste gasification, biomass gasification, pet coke gasification and coal gasification, gasification of lignin and associated streams, titanium dioxide production processes, cement production processes, natural gas power processes and coal fired power processes.

For example, the integration of a Basic oxygen furnace (BOF), with a fermentation unit, and an electrolysis unit provides a number of synergetic benefits. A typical BOF and fermentation integration comprises using the C1-containing tail-gas produced by the BOF process as a fermentation feedstock utilizing a C1-fixing microorganism. FIG. 1 shows a typical BOF process integration with a C1-utilizing fermentation. Air 10 is fed to an air separation unit 14, for example a cryogenic distillation unit or PSA, and the air is separated to provide an $O_2$ stream and a $N_2$ stream. The $N_2$ stream is removed from the separation unit via conduit 16. The $O_2$ is passed via a conduit 18 to a BOF unit 22. The BOF unit receives molten pig iron 20 (which is typically received from a Blast Furnace) and $O_2$. The treatment of the hot metal with $O_2$ results in the release of CO and $CO_2$ from carbon in the hot metal. The desired end product of the BOF process is recovered via conduit 24. The resultant gas stream comprising CO and $CO_2$ is passed from the BOF unit 22 via a conduit 26 to a gas treatment unit 28 wherein the gas undergoes at least one treatment process to remove any unwanted contaminants from the gas. The C1-containing gaseous substrate exiting the gas treatment unit 28 is passed to a bioreactor 32 via a conduit 30. The bioreactor 32 contains a culture of at least one C1-fixing microorganism in a liquid nutrient broth. The C1-Fixing bacteria utilize at least one C1-component in the C1-containing substrate, as a carbon source, and produce one or more fermentation products. The one or more fermentation produces are recovered from the fermentation broth via conduit 36. An exit gas comprising $CO_2$ and unreacted CO exits the bioreactor 32 as an exit gas via a vent conduit 34. A typical BOF process exit gas contains CO, $CO_2$ and nitrogen, with minimal amounts of hydrogen. An exemplary BOF exit gas stream composition is 50-70% CO, 15-25% $CO_2$, 15-25% $N_2$, and 0-5-3% $H_2$.

In the absence of sufficient $H_2$ in the C1-containing substrate, CO utilized by the C1-fixing bacteria is converted into ethanol and $CO_2$ as follows: $6CO+3H_2O \rightarrow C_2H_5OH+ 4CO_2$. Prior to integration of BOF processes with fermentation processes, the exit steam from the BOF process is typically used for electricity generation. The reaction stoichiometry of electricity production is: $6\ CO \rightarrow 6\ CO_2$+ electricity. The incorporation of a gas fermentation unit can reduce the total $CO_2$ emissions by up to 33% (compared to BOF processes with electricity generation).

The present invention, provides processes for improving the efficiency C1-generating industrial process and fermentation integration. Particularly, the present invention provides processes and systems for substantially reducing the total amount of CO2 emitted from an integrated facility.

Electrolysis products (e.g. hydrogen, carbon monoxide and oxygen) can also be utilized to improve overall efficiency of the integration of industrial production processes and gas fermentation processes e.g. in industrial processes where the C1-containing tail gas is suitable for use as a fermentation substrate, further substrate optimisation by blending with hydrogen or carbon monoxide can improve the over-all carbon utilisation of the fermentation. Efficiency can be improved by (i) using hydrogen to improve the fermentation substrate composition; (ii) using carbon monoxide to improve the fermentation substrate composition; (iii) using oxygen derived from the electrolysis process to offset the oxygen requirements of the industrial process; (iv) recycling $CO_2$ from the fermentation process exit gas stream to a $CO_2$ electrolyser to produce additional CO and further reduce $CO_2$ emissions; or (v) a combination of the above.

Hydrogen can be used to improve the fermentation substrate composition. Hydrogen provides energy required by the microorganism to convert carbon containing gases into useful products. When optimal concentrations of hydrogen are provided, the microbial culture is able to produce the desired fermentation products (i.e. ethanol) without any co-production of carbon dioxide.

Carbon monoxide produced by electrolysis of $CO_2$ can be used to improve the fermentation substrate composition, and can enrich the CO content of the industrial waste gas being utilized as a fermentation substrate. Additionally, any $CO_2$ produced by the fermentation process can be recycled as a feedstock for the $CO_2$ electrolyser, thereby further reducing $CO_2$ emissions and increasing the amount of carbon captured in liquid fermentation products.

In a number of these industrial processes, oxygen is sourced from an air feed. In partial oxidation processes, such as Basic oxygen furnace (BOF) processes; COREX or FINEX steel making processes, Blast Furnace (BF) processes, titanium dioxide production processes, ferroalloy production processes and gasification processes, $O_2$ is typically produced from air using an air separation process (e.g. cryogenic distillation or PSA separation). According to the present invention, $O_2$ produced by the electrolysis process, can reduce or replace the requirement for air separation.

Figure 2:
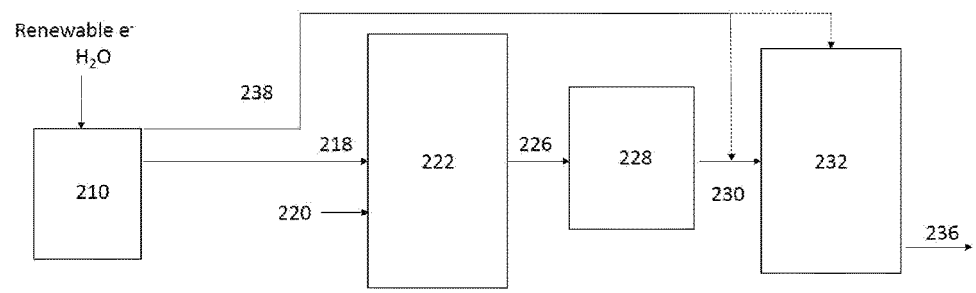
FIG. 2 shows a process integration scheme depicting integration of a Basic Oxygen Furnace process with a fermentation process and a water electrolysis process, in accordance with one aspect of the invention.

FIG. 2 is a schematic representation of the integrated systems and process according to one aspect of the invention. An electrolysis unit 210 receives renewable energy and water. Exemplary sources for the renewable energy include, but are not limited to wind power, hydropower, solar energy, geothermal energy, nuclear energy and combinations thereof. The energy and water produce hydrogen and oxygen according to the following reaction: 2 $H_2O$+electricity→2 $H_2$+$O_2$+heat. The $O_2$ produced by the electrolysis unit 210 is provided to the BOF unit 222 via a conduit 218. The BOF unit 222 also receives molten pig iron via conduit 220 (typically the molten pig iron is received from a Blast Furnace process). The $O_2$ is passed over the molten pig iron to produce steel, and an exit gas comprising CO and $CO_2$. The exit gas is passed via conduit 226 to a gas treatment unit 228, the gas treatment unit 228 comprising at least one gas treatment module for removal of one or more contaminants from the gas stream. The C1-containing substrate exiting the gas treatment unit 228 is passed to a bioreactor 232 via a conduit 230. In accordance with one aspect of the invention, hydrogen produced in the electrolysis unit 210 is passed to either the bioreactor or to an optional blending means via conduit 238. In a preferred embodiment, $H_2$ is blended with the C1-containing substrate prior to the C1-containing substrate being passed to the bioreactor 230. The bioreactor is operated at conditions to produce at least one fermentation product by the fermentation of the C1-containing substrate by a culture of C1-fixing bacterium. The fermentation products can be recovered via conduit 236. The system and process of FIG. 2, may further include a blending means (not shown) for blending the C1-containing substrate and the hydrogen stream produced by the electrolysis process. The hydrogen enriched C1-containing substrate is provided to the bioreactor 232. The composition of the hydrogen enriched C1-containing substrate and the amount of product generated, can be generally defined by the following equation;

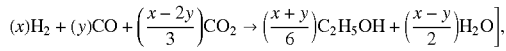

where x>2y for $CO_2$ consumption. In some instances, CO2 may be present in excess of the stoichiometric amount,

The invention described in FIG. 2, can be applied to a number of other industrial process, which involve a partial oxidation process. Exemplary integrations are provided below.

Blast Furnace (BF) and its Gas Supply and Gas Products: $H_2$ produced by electrolysis is combined with Blast Furnace tail gas to adjust the $H_2$:CO:$CO_2$ ratio in the C1-containing substrate. The resultant C1-containing substrate is provided to a fermentation process to produce ethanol or other chemicals. The $O_2$ produced by the electrolysis process is used to supply the oxygen requirements to the Blast Furnace. The $O_2$ produced by electrolysis would be sufficient to meet the oxygen requirements of the Blast Furnace, and minimizing $N_2$ (from enriching the $O_2$ feed) would enable the production of C1-gas enriched BF gases. The C1-enriched BF gases would have benefits for reducing the cost of fermentation of this combined gas stream.

Gasified Feedstocks and their Gas Supply and Gas Products: $H_2$ produced by electrolysis can be combined with gases from gasified biomass/municipal solid waste (MSW)/DSW/petroleum coke/coal/heavy oil/petroleum/solid fuels to adjust the $H_2$:CO:CO2 ratio in the C1-containing substrate. The resultant C1-containing substrate is provided to a fermentation process to produce ethanol or other products. The $O_2$ produced by electrolysis can be used to supply the oxygen requirements to the gasifier to enable the production of syngas with low nitrogen.

COREX/FINEX Steelmaking and their Gas Supply and Gas Products: $H_2$ produced by electrolysis can be combined with COREX/FINEX tail gases to adjust the $H_2$:CO:$CO_2$ ratio of the C1-containing substrate. The resultant C1-containing substrate is provided to a fermentation process to produce ethanol or other products. The $O_2$ produced by electrolysis can be used to supply the oxygen requirements to the COREX unit.

Titanium Dioxide and their Gas Supply and Gas Products: $H_2$ produced by electrolysis can be combined with titanium dioxide production process tail gases to adjust the $H_2$:CO:$CO_2$ ratio of the C1-containing substrate. The resultant C1-containing substrate is provided to a fermentation process to produce ethanol or other products. The $O_2$ produced by electrolysis can be used to supply the oxygen requirements to the titanium dioxide production unit.

In one aspect the invention provides an integrated process for producing one or more products, the process comprising; producing hydrogen by electrolysis; blending at least a portion of the produced hydrogen with a gaseous stream comprising at least one C1 gas to provide a blended gaseous stream; passing the blended gaseous stream to a bioreactor containing a culture of at least one C1 fixing bacterium; and fermenting the culture to produce one or more fermentation products. In certain embodiments, the fermentation process further produces an exit gas stream comprising $CO_2$.

In one embodiment, the invention provides an integrated process comprising: producing $H_2$ and $O_2$ by electrolysis of water using a renewable energy source; providing at least a portion of the produced $O_2$ to a C1-generating industrial process; operating the C1-generating industrial process under conditions to generate a tail gas comprising at least one C1-component, blending at least a portion of the tail gas comprising at least one C1-component with at least a portion of the produced hydrogen to provide a C1-containing gaseous substrate; passing the C1-containing gaseous substrate to a bioreactor containing a culture of C1-fixing bacterium; and fermenting the C1-containing gaseous substrate to produce at least one fermentation product.

In one embodiment, the invention provides an integrated process comprising: producing $H_2$ and $O_2$ by electrolysis of water using a renewable energy source, providing at least a portion of the produced $O_2$ to a partial oxidation process, generating a C1-containing tail gas by partial oxidation, blending at least a portion of the C1-containing tail gas with at least a portion of the produced $H_2$ to provide a C1-containing substrate, passing the C1-containing substrate to a bioreactor containing a culture of C1-fixing bacterium, and fermenting the C1-containing substrate to produce at least one fermentation product.

In some instances the gas compositions of the C1 containing gases are not ideal for the fermentation process of the current invention. Due to geological restrictions, lack of available hydrogen sources, or cost consideration, the use of the gases for fermentation processes has not been feasible. By utilizing renewable hydrogen (e.g hydrogen produced by electrolysis), a number of these restrictions can be reduced or removed. Furthermore, blending C1 containing gas with a renewable hydrogen stream, provides an energetically improved blended substrate stream.

A number of industrial processes producing C1 containing gases, which are not ideal for the C1 fermentation processes disclosed herein have been identified, and include Cement production processes, natural gas power plants, refinery processes, and ethanol bioreactor fermentation processes. Cement production process typically produce $CO_2$ rich exit gas streams. $CO_2$ can be utilised by C1-fixing microorganism, however hydrogen is required to provide the energy required for fixing $CO_2$ into products.

The integration of a complete oxidation process, such as a cement production process, with a $CO_2$ electrolyser and a C1-fixing fermentation process provides a number of synergistic benefits including (i) providing a mechanism for converting $CO_2$ to CO, which is an energetically preferred fermentation substrate; (ii) $O_2$ provided by the electrolysis process displaces the air feed to the cement production process with and increases the composition of $CO_2$ in the exit gas of the cement production process; (iii) $CO_2$ produced by the fermentation process can be recycled to the $CO_2$ electrolyser and converted to CO substrate for fermentation, thereby further decreasing $CO_2$ emissions by the combined processes.

Figure 3:
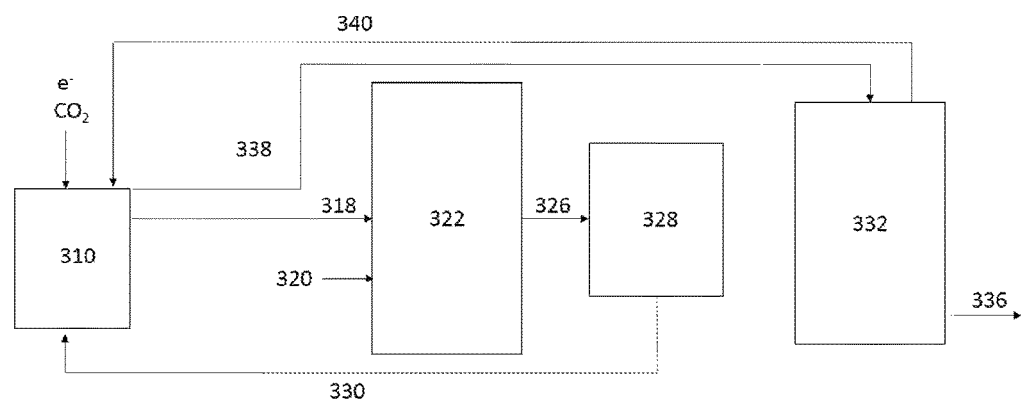
FIG. 3 shows a process integration scheme depicting integration of a cement production process with a fermentation process and a carbon dioxide electrolysis process, in accordance with one aspect of the invention.

FIG. 3 is a schematic representation of the integrated systems and process according to one aspect of the invention. An electrolysis unit 310 receives energy and carbon dioxide. Exemplary sources for the renewable energy include, but are not limited to wind power, hydropower, solar energy, geothermal energy, nuclear energy and combinations thereof. The energy and $CO_2$ produce carbon monoxide and $O_2$ according to the following reaction: 2 $CO_2$+electricity→2 $CO+O_2$+heat. The $O_2$ produced by the electrolyser 310 is provided to the cement production unit 322 via a conduit 318, to displace the air requirement of the cement production process. The tail gas comprising $CO_2$ is passed via conduit 326 to a gas treatment unit 328. The gas treatment unit 328 comprises at least one gas treatment module for removal of one or more contaminants from the gas stream. The C1-containing substrate exiting the gas treatment unit 328 is passed to the electrolyser 310 via a conduit 330. In accordance with one aspect of the invention, carbon monoxide produced in the electrolyser 310 is passed to bioreactor 332 via conduit 338. In certain embodiments, hydrogen can be provided to the bioreactor, or blended with CO stream prior to the CO stream being passed to the bioreactor. The bioreactor is operated at conditions to produce at least one fermentation product by the fermentation of the C1-containing substrate by a culture of C1-fixing bacterium. The fermentation products can be recovered via conduit 336. The fermentation process further produces an exit gas comprising $CO_2$. In preferred embodiments, at least a portion of the $CO_2$ in the exit gas stream is passed to the $CO_2$ electrolyser, via conduit 340, as a feedstock for the $CO_2$ electrolysis process.

In another aspect, the invention provides an integrated process comprising: producing CO and $O_2$ by electrolysis of carbon dioxide, providing at least a portion of the produced $O_2$ to a C1-generating industrial process, operating the C1-generating industrial process under conditions to generate a tail gas comprising at least one C1-component, blending at least a portion of the produced CO with the C1-component of the tail gas to provide a blended C1-containing substrate, passing the blended C1-containing substrate to a bioreactor containing a culture of C1-fixing bacterium, and fermenting the blended C1-containing substrate to produce at least one fermentation product.

In one embodiment, the invention provides an integrated process comprising: producing CO and $O_2$ by electrolysis of carbon dioxide, providing at least a portion of the produced $O_2$ to a partial oxidation process, generating a C1-containing tail gas by partial oxidation, blending at least a portion of the produced CO with at least a portion of the C1-containing tail gas to provide a blended C1-containing substrate, passing the blended C1-containing substrate to a bioreactor containing a culture of C1-fixing bacterium, and fermenting the C1-containing substrate to produce at least one fermentation product.

The partial oxidation process, is an industrial process comprising a partial oxidation reaction. The partial oxidation process is selected from the group consisting of a Basic oxygen furnace (BOF) reaction, a COREX or FINEX steel making process, a Blast Furnace (BF) process, a ferroalloy process; a titanium dioxide production process and a gasification processes. The gasification process is selected from the group consisting of a municipal solid waste gasification process, a biomass gasification process, a pet coke gasification process, and, a coal gasification process. In a preferred embodiment, the partial oxidation process is a BOF process.

The C1-containing tail gas comprises at least one C1-component. The C1-component in the C1-containing tail gas is selected from the group consisting of carbon monoxide, carbon dioxide, methane and combinations thereof. The C1-containing tail gas may further comprise one or more non-C1 components, such as nitrogen and hydrogen. The C1-containing tail gas may further comprise toxic or contaminant components from the industrial process. In a preferred embodiment, the C1-containing tail gas is passed to a gas treatment unit for the removal of at least one contaminant or non-C1 component, to provide a purified C1-containing tail gas, prior to being passed to the bioreactor.

In an alternative embodiment, the invention provides an integrated process comprising producing CO and $O_2$ by electrolysis of $CO_2$, providing at least a portion of the produced $O_2$ to a complete oxidation process, generating a $CO_2$-containing tail gas by complete oxidation, passing at least a portion of the $CO_2$-containing tail gas to the electrolysis process as a feedstock; passing at least a portion of the produced CO to a bioreactor containing a culture of C1-fixing bacterium, and fermenting the CO to produce at least one fermentation product and a bioreactor tail gas stream comprising $CO_2$. Preferably, at least a portion of the bioreactor tail gas stream comprising $CO_2$ is recycled to the $CO_2$ electrolysis process.

The integration of a cement production process with a water electrolysis process enables an energetically improved gaseous substrate. The integration has two benefits, (i) displacing the air feed to the cement production process with $O_2$ from the electrolysis process, increases the composition of $CO_2$ in the exit gas of the cement production process, and (ii) the blending of hydrogen produced by the electrolysis process with the $CO_2$ rich gas produced provides a $CO_2$ and $H_2$ gas stream suitable for fermentation processes.

In particular aspects of the invention, at least a first portion of the $CO_2$ from the cement production process and a first portion of the hydrogen from the electrolysis process can be provided to a reverse water-gas shift process (RWGS) to produce CO by the following stoichiometric reaction:

$$CO_2 + H_2 \leftrightarrow CO + H_2O$$

The CO produced by the RWGS, can be blended with a second portion of the $CO_2$ derived from the industrial gas stream and a second portion of the produced hydrogen to provide a fermentation substrate having a desired composition. The desired composition of the fermentation substrate will vary depending on the desired fermentation product of the fermentation reaction. For ethanol production, for example, the desired composition can be determined by the following formula:

$$(x)H_2 + (y)CO + \left(\frac{x-2y}{3}\right)CO_2 \rightarrow \left(\frac{x+y}{6}\right)C_2H_5OH + \left(\frac{x-y}{2}\right)H_2O,$$

where x>2y for CO2 consumption. In certain embodiments, the fermentation substrate may have a $H_2$:CO ratio of less than 20:1 or less than 15:1 or less than 10:1 or less than 8:1 or less than 5:1 or less than 3:1 with $CO_2$ available in at least stoichiometric amounts according to algebraic formula.

In other embodiments, the invention provides an integrated process comprising: producing $H_2$ and $O_2$ by electrolysis of water using a renewable energy source, providing at least a portion of the produced $O_2$ to a complete oxidation process, generating a C1-containing tail gas by complete oxidation; blending at least a portion of the C1-containing tail gas with at least a portion of the produced $H_2$ to provide a C1-containing substrate, passing the C1-containing substrate to a bioreactor containing a culture of C1-fixing bacterium, and fermenting the C1-containing substrate to produce at least one fermentation product.

The complete oxidation process is selected from the group consisting of a cement production process, a natural gas power process and a coal fired power process. The C1-containing tail gas produced by complete oxidation comprises $CO_2$. In some embodiments the C1-containing tail gas produced by complete oxidation further comprises at least one component selected from the group consisting of $H_2$, CO and $CH_4$.

Figure 4:
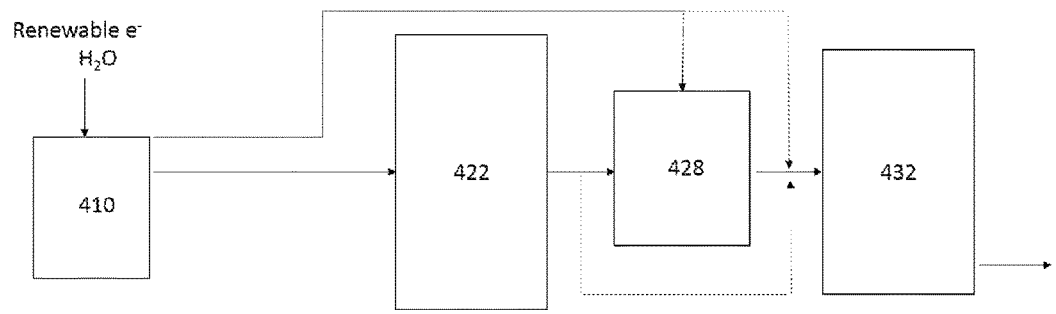
FIG. 4 shows a schematic process for the integration of a cement production process with an electrolysis process and a gas fermentation process.

FIG. 4 shows a schematic process for the integration of a cement production process with an electrolysis process and a gas fermentation process. $H_2$ and $O_2$ are produced by electrolysis of renewable energy and water in an electrolysis unit 410. The produced $O_2$ is provided to a cement production unit 422, to displace the air requirement of the cement production process. The cement production process produces a $CO_2$ rich tail gas. A first portion of the $CO_2$ rich tail gas from the cement production process, and a first portion of the hydrogen from the electrolysis process are sent to a Reverse Water Gas Shift Reactor 428. The $CO_2$ and $H_2$ are reacted to produce an exit stream comprising CO. A second portion of the $CO_2$ rich tail gas from the cement production process, and a second portion of the hydrogen from the electrolysis process are blended with the CO rich exit gas from the RWGS reactor to provide a C1-containing substrate. The C1-containing substrate is passed to a bioreactor 432 containing a culture of C1-fixing bacteria. The C1-containing substrate is fermented to produce at least one fermentation product.

A "C1-fixing microorganism" is a microorganism that has the ability to produce one or more products from a C1-carbon source. Typically, the microorganism is a C1-fixing bacterium. In a preferred embodiment, the microorganism is or is derived from a C1-fixing microorganism identified in Table 1. The microorganism may be classified based on functional characteristics. For example, the microorganism may be or may be derived from a C1-fixing microorganism, an anaerobe, an acetogen, an ethanologen, and/or a carboxydotroph. Table 1 provides a representative list of microorganisms and identifies their functional characteristics.

TABLE 1

|  | C1-fixing | Anaerobe | Acetogen | Ethanologen | Autotroph | Carboxydotroph | Methanotroph |
|---|---|---|---|---|---|---|---|
| *Acetobacterium woodii* | + | + | + | +/−[1] | − | +/−[2] | − |
| *Alkalibaculum bacchii* | + | + | + | + | + | + | − |
| *Blautia* product | + | + | + | − | + | + | − |
| *Butyribacterium methylotrophicum* | + | + | + | + | + | + | − |
| *Clostridium aceticum* | + | + | + | − | + | + | − |
| *Clostridium autoethanogenum* | + | + | + | + | + | + | − |
| *Clostridium carboxidivorans* | + | + | + | + | + | + | − |
| *Clostridium coskatii* | + | + | + | + | + | + | − |
| *Clostridium drakei* | + | + | + | − | + | + | − |
| *Clostridium formicoaceticum* | + | + | + | − | + | + | − |
| *Clostridium ljungdahlii* | + | + | + | + | + | + | − |
| *Clostridium magnum* | + | + | + | − | + | +/−[3] | − |
| *Clostridium ragsdalei* | + | + | + | + | + | + | − |

TABLE 1-continued

|  | C1-fixing | Anaerobe | Acetogen | Ethanologen | Autotroph | Carboxydotroph | Methanotroph |
|---|---|---|---|---|---|---|---|
| *Clostridium scatologenes* | + | + | + | − | + | + | − |
| *Eubacterium limosum* | + | + | + | − | + | + | − |
| *Moorella thermautotrophica* | + | + | + | + | + | + | − |
| *Moorella thermoacetica* (formerly *Clostridium thermoaceticum*) | + | + | + | −[4] | + | + | − |
| *Oxobacter pfennigii* | + | + | + | − | + | + | − |
| *Sporomusa ovata* | + | + | + | − | + | +/−[5] | − |
| *Sporomusa silvacetica* | + | + | + | − | + | +/−[6] | − |
| *Sporomusa sphaeroides* | + | + | + | − | + | +/−[7] | − |
| *Thermoanaerobacter kiuvi* | + | + | + | − | + | − | − |

[1]*Acetobacterium woodi* can produce ethanol from fructose, but not from gas.
[2]It has been reported that *Acetobacterium woodi* can grow on CO, but the methodology is questionable.
[3]It has not been investigated whether *Clostridium magnum* can grow on CO.
[4]One strain of *Moorella thermoacetica*, *Moorella* sp. HUC22-1, has been reported to produce ethanol from gas.
[5]It has not been investigated whether *Sporomusa ovata* can grow on CO.
[6]It has not been investigated whether *Sporomusa silvacetica* can grow on CO.
[7]It has not been investigated whether *Sporomusa sphaeroides* can grow on CO.

"C1" refers to a one-carbon molecule, for example, CO or $CO_2$. "C1-oxygenate" refers to a one-carbon molecule that also comprises at least one oxygen atom, for example, CO or $CO_2$. "C1-carbon source" refers a one carbon-molecule that serves as a partial or sole carbon source for the microorganism. For example, a C1-carbon source may comprise one or more of CO, $CO_2$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism is a C1-fixing bacterium. In a preferred embodiment, the microorganism is or is derived from a C1-fixing microorganism identified in Table 1.

An "anaerobe" is a microorganism that does not require oxygen for growth. An anaerobe may react negatively or even die if oxygen is present above a certain threshold. Typically, the microorganism is an anaerobe (i.e., is anaerobic). In a preferred embodiment, the microorganism is or is derived from an anaerobe identified in Table 1.

An "acetogen" is a microorganism that produces or is capable of producing acetate (or acetic acid) as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). Acetogens use the acetyl-CoA pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, N.Y., 2006). All naturally occurring acetogens are C1-fixing, anaerobic, autotrophic, and non-methanotrophic. In a preferred embodiment, the microorganism is an acetogen. In a preferred embodiment, the microorganism is or is derived from an acetogen identified in Table 1.

An "ethanologen" is a microorganism that produces or is capable of producing ethanol. In a preferred embodiment, the microorganism is an ethanologen. In a preferred embodiment, the microorganism is or is derived from an ethanologen identified in Table 1.

An "autotroph" is a microorganism capable of growing in the absence of organic carbon. Instead, autotrophs use inorganic carbon sources, such as CO and/or $CO_2$. In a preferred embodiment, the microorganism is an autotroph. In a preferred embodiment, the microorganism is or is derived from an autotroph identified in Table 1.

A "carboxydotroph" is a microorganism capable of utilizing CO as a sole source of carbon. In a preferred embodiment, the microorganism is a carboxydotroph. In a preferred embodiment, the microorganism is or is derived from a carboxydotroph identified in Table 1.

In certain embodiments, the microorganism does not consume certain substrates, such as methane or methanol. In one embodiment, the microorganism is not a methanotroph and/or is not a methylotroph.

More broadly, the microorganism may be or may be derived from any genus or species identified in Table 1. For example, the microorganism may be a member of the genus *Clostridium*.

In a preferred embodiment, the microorganism is or is derived from the cluster of Clostridia comprising the species *Clostridium autoethanogenum*, *Clostridium ljungdahlii*, and *Clostridium ragsdalei*. These species were first reported and characterized by Abrini, *Arch Microbiol*, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 μm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut,

*Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22: 320-325, 2011).

Thus, in summary, many of the characteristics of *Clostridium autoethanogenum, Clostridium ljungdahlii,* or *Clostridium ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism may also be or be derived from an isolate or mutant of *Clostridium autoethanogenum, Clostridium ljungdahlii,* or *Clostridium ragsdalei*. Isolates and mutants of *Clostridium autoethanogenum* include JA1-1 (DSM10061) (Abrini, *Arch Microbiol*, 161: 345-351, 1994), LBS1560 (DSM19630) (WO 2009/064200), and LZ1561 (DSM23693). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

The term "derived from" refers to a microorganism modified or adapted from a different (e.g., a parental or wild-type) microorganism, so as to produce a new microorganism. Such modifications or adaptations typically include insertion, deletion, mutation, or substitution of nucleic acids or genes.

Substrate" refers to a carbon and/or energy source for the microorganism of the invention. Typically, the substrate is gaseous and comprises a C1-carbon source, for example, $CO$, $CO_2$, and/or $CH_4$. Preferably, the substrate comprises a C1-carbon source of $CO$ or $CO+CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or basic oxygen furnace gas), about 20-30 mol % CO (e.g., blast furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no (<1 mol %) $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no (<1 mol %) $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a by-product of an industrial process or from some other source, biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

In particular embodiments, the industrial process is a steel manufacturing process selected from Basic Oxygen Furnace, Blast Furnace and Coke Oven processes. Coke oven gas (COG) has a typical composition of 5-10% CO, 55% $H_2$, 3-5% $CO_2$, 10% $N_2$ and 25% $CH_4$. The typical composition of Blast furnace (BF) gas is 20-35% CO, 2-4% $H_2$, 20-30% $CO_2$ and 50-60% $N_2$. A typical Basic oxygen furnace (BOF) gas comprises 50-70% CO, 15-25% $CO_2$, 15-25% $N_2$ and 1-5% $H_2$.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The composition of the C1-containing gaseous substrate will vary according to factors including the type of industrial process used, and the feedstock provided to the industrial process. Not all C1 containing gaseous substrates produced will have an ideal gas composition for a fermentation process. The blending of the C1 containing gases with a renewable hydrogen stream, an additional CO stream or converting $CO_2$ in the C1 substrate to CO, provides an energetically improved blended gas stream.

Operating the fermentation process in the presence of hydrogen, has the added benefit of reducing the amount of $CO_2$ produced by the fermentation process. For example, a gaseous substrate comprising minimal H2, will typically produce ethanol and CO2 by the following stoichiometry [6

CO+3 H$_2$O→C$_2$H$_5$OH+4 CO$_2$]. As the amount of hydrogen utilized by the C1 fixing bacterium increase, the amount of CO$_2$ produced decreases [e.g., 2 CO+4 H$_2$→C$_2$H$_5$OH+H$_2$O]. The general form of the equation is:

$$(x)H_2 + (y)CO + \left(\frac{x-2y}{3}\right)CO_2 \to \left(\frac{x+y}{6}\right)C_2H_5OH + \left(\frac{x-y}{2}\right)H_2O,$$

where x>2y to achieve CO2 consumption.

When CO is the sole carbon and energy source for ethanol production, a portion of the carbon is lost to CO$_2$ as follows:

6CO+3H$_2$O→C$_2$H$_5$OH+4CO$_2$ (ΔG°=−224.90 kJ/mol ethanol)

In these cases, where a substantial amount of carbon is being diverted to CO$_2$, it is desirable to pass the CO$_2$ either back to the industrial process (i.e. in a gasification process) or alternatively to send the CO$_2$ to a reverse water gas shift reactor. In accordance with the present invention, when a CO$_2$ electrolyser is present, the CO$_2$ tail gas can be recycled to the electrolyser for reduction to CO and O$_2$.

As the amount of H$_2$ available in the substrate increases, the amount of CO$_2$ produced decreases. At a stoichiometric ratio of 1:2 (CO/H$_2$), CO$_2$ production is completely avoided 5CO+1H$_2$+2H$_2$O→1C$_2$H$_5$OH+3CO$_2$ (ΔG°=−204.80 kJ/mol ethanol)

4CO+2H$_2$+1H$_2$O→1C$_2$H$_5$OH+2CO$_2$ (ΔG°=−184.70 kJ/mol ethanol)

3CO+3H$_2$→1C$_2$H$_5$OH+1CO$_2$ (ΔG°=−164.60 kJ/mol ethanol)

In a fermentation, where CO$_2$ is the carbon source and H$_2$ is the electron source, the stoichiometry is as follows 2CO$_2$+6H2→C$_2$H$_5$OH+3H$_2$O (ΔG°=−104.30 kJ/mol ethanol)

The O$_2$ by-product of the electrolysis production process may be used in the industrial process for the production of the CO$_2$ gas. In the case of complete oxidation processes, the O$_2$ by-product of the electrolysis would replace the air feed typically required. Addition of oxygen rather than air increases the composition of CO$_2$ in the exit gas of the process. For example, a 100% oxygen fed: CH$_4$+2 O$_2$→CO$_2$+2H$_2$O provides 100% CO$_2$ concentration in the exit gas; whereas air fed: CH$_4$+2 O$_2$+7.5 N$_2$→CO$_2$+2H$_2$O+7.5 N$_2$ provides 12% CO$_2$ in the exit gas.

The CO$_2$ feedstock can be blended with hydrogen produced by electrolysis to provide an optimized feedstock for a CO$_2$ and H$_2$ fermentation process. [e.g., 6 H$_2$+2 CO$_2$→C$_2$H$_5$OH+3 H$_2$O]

The C1 fixing bacterium is typically an anaerobic bacterium selected from the group consisting of carboxydotrophs, autotrophs, acetogens, and ethanologens. More particularly the C1 fixing bacterium is selected from the genus *Clostridium*. In particular embodiments, the C1 fixing bacterium is selected from the group consisting of *Clostridium autoethanogenum*, *Clostridium ljungdahlii*, and *Clostridium ragsdalei*.

The microorganism of the invention may be cultured to produce one or more products. For instance, *Clostridium autoethanogenum* produces or can be engineered to produce ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2013/036147), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/0369152), and 1-propanol (WO 2014/0369152). In addition to one or more target products, the microorganism of the invention may also produce ethanol, acetate, and/or 2,3-butanediol. In certain embodiments, microbial biomass itself may be considered a product.

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism, but is not produced by a genetically unmodified microorganism from which the genetically modified microorganism is derived.

"Increasing the efficiency," "increased efficiency," and the like include, but are not limited to, increasing growth rate, product production rate or volume, product volume per volume of substrate consumed, or product selectivity. Efficiency may be measured relative to the performance of parental microorganism from which the microorganism of the invention is derived.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor.

EXAMPLES

The following examples further illustrate the invention but, of course, should not be construed to limit its scope in any way.

Example 1

This example describes the integration of a Basic Oxygen Furnace (BOF) process with an electrolysis process and a fermentation process, to provide a fermentation substrate having an improved composition, thereby resulting in an improved fermentation product yield.

The BOF process produces a BOF tail gas having the following composition: 50-70% CO, 15-25% $CO_2$, 15-25% $N_2$, and 0-5-3% $H_2$.

The electrolysis process produces hydrogen and oxygen as follows: $2H_2O + electricity \rightarrow 2H_2 + O_2 + heat$.

The oxygen produced by the electrolysis process if provided the BOF to offset the oxygen requirement.

The hydrogen produced by the electrolysis process is blended with the BOF tail gas to provide a fermentation substrate comprising $H_2:CO:CO_2$ ratio of 10:3.5:1. The fermentation substrate is provided to a bioreactor containing a culture of *Clostridium autoethanogenum* strain deposited at the DSMZ under the accession number DSM23693.

The overall process stoichiometry of the reaction is as follows:

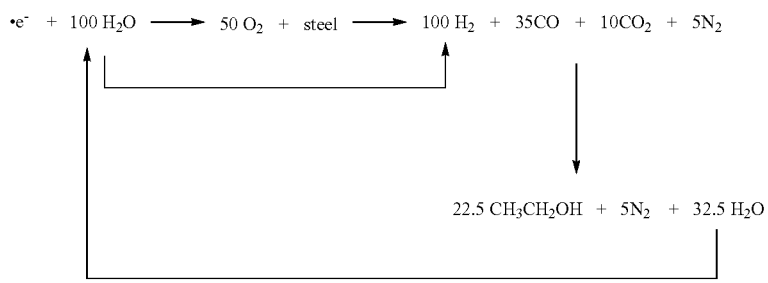

The provision of a process integration an electrolysis process, with a BOF process and fermentation process, results in the production of ethanol, and the mitigation of $CO_2$ as a waste product.

Example 2

This example describes the integration of a Basic Oxygen Furnace (BOF) process with an electrolysis process and a fermentation process, to provide a fermentation substrate having an improved composition, thereby resulting in an improved fermentation product yield.

The BOF process produces a BOF tail gas having the following composition: 50-70% CO, 15-25% $CO_2$, 15-25% $N_2$, and 0-5-3% $H_2$.

The electrolysis process produces carbon monoxide and oxygen as follows: $2CO_2 + electricity \rightarrow 2CO + O_2 + heat$.

The oxygen produced by the electrolysis process if provided the BOF to offset the oxygen requirement.

The carbon monoxide produced by the electrolysis process is blended with the BOF tail gas to provide a fermentation substrate comprising $H_2:CO:CO_2$ ratio of [ratio needed]. The fermentation substrate is provided to a bioreactor containing a culture of *Clostridium autoethanogenum* strain deposited at the DSMZ under the accession number DSM23693. The substrate is fermented to produce one or more fermentation products, including ethanol, and a tail gas stream. $CO_2$ from the bioreactor tail gas stream is captured and sent to a $CO_2$ electrolysis unit, the produced CO is recycled back to the fermenter, and the produced $O_2$ is recycled back to steelmaking. The 100% O2 for steelmaking displaces other sources of $O_2$ (typically 94% $O_2$, 6% $N_2$) which reduces the N2 in the steelmaking offgases and enriches the gases, improving both process units.

The overall process stoichiometry of the reaction is as follows:

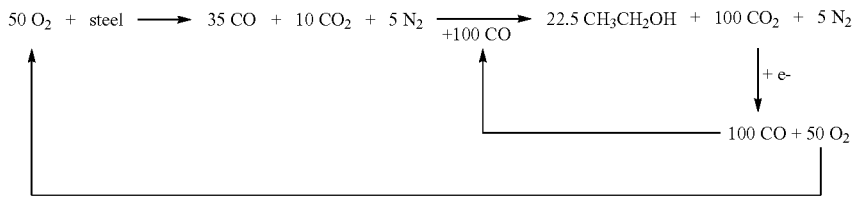

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods or processes described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for improving carbon capture efficiency in an integrated fermentation and industrial process, wherein the process comprises:
   i. passing one or more feedstocks comprising $CO_2$ to an electrolysis process to produce an electrolysis derived substrate comprising CO and $O_2$;
   ii. blending at least a portion of the electrolysis derived substrate with a C1-containing tail gas from an industrial process to provide a blended C1-containing substrate;
   iii. passing the blended C1-containing substrate to a bioreactor containing a culture of at least one anaerobic C1-fixing bacterium; and
   iv. anaerobically fermenting the culture to produce one or more fermentation products.

2. The process of claim 1, wherein at least a portion of the $O_2$ is passed to the industrial process.

3. The process of claim 1, wherein an exit gas stream is produced by the fermentation, the exit gas comprises $CO_2$, and at least a portion of the $CO_2$ is recycled to the electrolysis process.

4. The process of claim 1, wherein the electrolysis process requires an energy input, and the energy input is derived from a renewable energy source.

5. The process of claim 1 wherein the industrial process is a partial oxidation process, wherein said partial oxidation process is selected from the group consisting of a Basic oxygen furnace (BOF) reaction; a COREX or FINEX steel making process, a Blast Furnace (BF) process, a ferroalloy process; a titanium dioxide production process and a gasification process.

6. The process of claim 5, wherein the partial oxidation process is a gasification process, and wherein the gasification process is selected from the group consisting of a municipal solid waste gasification process, a biomass gasification process, a pet coke gasification process and a coal gasification process.

7. The process of claim 1 wherein the industrial process comprises a complete oxidation process selected from the group consisting of cement production processes, natural gas power plants, and coal fired power plants.

8. The process of claim 1, wherein the C1-containing tail gas comprises CO, $CO_2$ and $H_2$.

9. The process of claim 1, wherein the blended C1-containing substrate comprises CO.

10. The process of claim 9, wherein the blended C1-containing substrate further comprises at least one component selected from the group consisting of $CO_2$, $H_2$, $CH_4$.

11. The process of claim 1, wherein the C1 fixing bacteria are selected from the genus *Clostridium*.

12. The process of claim 11, wherein the at least one C1 fixing bacterium is selected from the group consisting of *Clostridium autoethanogenum, Clostridium ljungdahlii*, and *Clostridium ragsdalei*.

13. The process of claim 2, wherein a portion of the C1-containing tail gas is blended with a portion of the oxygen from the electrolysis unit to match the oxygen richness required for the feed to the industrial process.

14. The process of claim 1, wherein the at least one fermentation product is selected from the group consisting of ethanol, acetate, butanol, butyrate, 2,3-butanediol, lactate, butene, butadiene, methyl ethyl ketone, ethylene, acetone, isopropanol, lipids, 3-hydroxypropionate, isoprene, fatty acids, 2-butanol, 1,2-propanediol, and 1-propanol.

15. An integrated system comprising;
   i. an electrolyser for producing an electrolysis derived substrate comprising CO and $O_2$;
   ii. an industrial process zone, utilizing at least a portion of an electrolysis derived substrate of (i) and generating C1-containing tail gas;
   iii. an anaerobic fermentation zone producing at least one fermentation product by anaerobic fermentation of at least a portion of the industrial waste gas of (ii) by an anaerobic C1-fixing bacteria.

16. The system of claim 15, wherein the system further comprises a blending unit, for blending a portion of an electrolysis derived substrate from the electrolysis unit with at least a portion of the C1-containing tail gas to produce a blended C1-containing substrate, and a conduit for passing the blended C1-containing substrate from the blending unit, to the fermentation unit.

17. The system of claim 15 wherein the energy source for the electrolysis unit is provided by a renewable energy production unit.

\* \* \* \* \*